(12) United States Patent
Paulus et al.

(10) Patent No.: US 6,399,951 B1
(45) Date of Patent: Jun. 4, 2002

(54) SIMULTANEOUS CT AND SPECT TOMOGRAPHY USING CZT DETECTORS

(75) Inventors: Michael J. Paulus, Knoxville, TN (US); Hamed Sari-Sarraf, Lubbock, TX (US); Michael L. Simpson, Knoxville, TN (US); Charles L. Britton, Jr., Alcoa, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/496,880

(22) Filed: Feb. 2, 2000

(51) Int. Cl.[7] ............................................... G01T 1/161
(52) U.S. Cl. ........................ 250/370.13; 250/363.04
(58) Field of Search ...................... 250/363.04, 370.01, 250/370.09, 370.13

(56) References Cited

U.S. PATENT DOCUMENTS

| | | |
|---|---|---|
| 4,060,822 A | 11/1977 | Jantsch et al. |
| 5,245,191 A | 9/1993 | Barber et al. |
| 5,512,756 A | 4/1996 | Bayer et al. |
| 5,528,495 A | 6/1996 | Roscoe |
| 5,739,540 A | 4/1998 | Motomura .............. 250/363.04 |
| 5,742,060 A | 4/1998 | Ashburn ................. 250/370.09 |
| 5,757,006 A | 5/1998 | DeVito et al. ............... 250/366 |
| 5,936,247 A | 8/1999 | Lange et al. ........... 250/363.03 |

*Primary Examiner*—Georgia Epps
*Assistant Examiner*—Richard Hanig
(74) *Attorney, Agent, or Firm*—Akerman Senterfitt

(57) ABSTRACT

A method for simultaneous transmission x-ray computed tomography (CT) and single photon emission tomography (SPECT) comprises the steps of: injecting a subject with a tracer compound tagged with a γ-ray emitting nuclide; directing an x-ray source toward the subject; rotating the x-ray source around the subject; emitting x-rays during the rotating step; rotating a cadmium zinc telluride (CZT) two-sided detector on an opposite side of the subject from the source; simultaneously detecting the position and energy of each pulsed x-ray and each emitted γ-ray captured by the CZT detector; recording data for each position and each energy of each the captured x-ray and γ-ray; and, creating CT and SPECT images from the recorded data. The transmitted energy levels of the x-rays lower are biased lower than energy levels of the γ-rays. The x-ray source is operated in a continuous mode. The method can be implemented at ambient temperatures.

26 Claims, 6 Drawing Sheets

SIMULTANEOUS CT AND SPECT TOMOGRAPHY USING CZT DETECTORS

STATEMENT REGARDING FEDERALLY SPONSORED RESEARCH AND DEVELOPMENT

This invention was made with government support under contract DE-AC05-96OR22464, awarded by the United States Department of Energy to Lockheed Martin Energy Research Corporation, and the United States Government has certain rights in this invention.

CROSS-REFERENCE TO RELATED APPLICATION

Not Applicable

BACKGROUND OF THE INVENTION

1. Field of the Invention

The invention relates generally to the fields of x-ray computed tomography (CT) studies and single photon emission tomography (SPECT) nuclear medicine studies, and in particular, to a computed tomography system suitable for simultaneous transmission x-ray computed tomography (CT) studies and single photon emission tomography (SPECT) nuclear medicine studies, with substantially increased spatial resolution.

2. Description of Related Art

Traditional computed tomography detectors employ silicon diodes or photo multiplier tubes coupled to scintillators. These detectors operate in current mode where the product of the mean x-ray event rate and the average x-ray energy is the measured parameter. These detectors are well suited for high count rate studies where high x-ray fluxes are employed, but they do not provide information about the energy of the individual x-ray energies. As a consequence, no energy dependent processing (such as multi-spectral image analysis or scatter correction) may be performed. The system disclosed here operates in "pulse mode"[2] where each x-ray is individually counted and its energy is recorded. The inclusion of energy (or spectral) data in the image provides improved soft tissue differentiation, reduces the effects of beam hardening and permits some degree of correction for scattered x-rays in the image.

Photon counting systems have been developed elsewhere using pixelated high purity germanium (HPGe) detectors. The, HPGe systems have many of the advantages described here, but require detector cooling, typically to 77° K. Pixelated detectors also have the disadvantage of requiring an electronic channel for each pixel. The CZT detectors employed here operate at room temperature and require less volume than HPGe due to their higher atomic number. Furthermore, the strip detector configuration requires only 2N electronic channels for $N^2$ pixels.

SUMMARY OF THE INVENTION

A novel computed tomography system suitable for simultaneous transmission x-ray computed tomography (CT) studies and single photon emission tomography (SPECT) nuclear medicine studies overcomes the problems of the prior art. The system employs cadmium zinc telluride (CZT) two-sided strip detectors (2SSD) to detect both x-rays and gamma rays (γ-rays). The x-ray CT measurements provide very high resolution images (<50 µm FWHM) of the laboratory animal's physical structure while the SPECT measurements provide lower resolution (~5 mm FWHM) functional images of the laboratory animal's metabolic activities. Both the CT and SPECT images are acquired in "pulse mode" where each x-ray or γ-ray is individually detected and its position and energy are individually recorded. Because the same mechanical assembly and detector are used for both CT and SPECT studies, the two types of measurement may be performed simultaneously and displayed in a single image. Previous technologies for combining images from different imaging modalities required two separate imaging systems and complex algorithms for post-acquisition registration of the images. Furthermore, unlike traditional CT data acquisitions which do not record the energies of the individual x-rays, this system can perform multi spectral analysis of the x-ray data set providing an opportunity for beam hardening correction and separation of soft tissue image data from skeletal tissue data. Finally, the 2SSD detector configuration requires only 2N electronic channels per $N^2$ pixels compared with standard pixelated detectors requiring one electronic channel for each pixel.

Researchers at Brookhaven National Laboratory have used monoenergetic x-ray beams from synchrotron x-ray sources. They have demonstrated that the use of monoenergetic sources improves image contrast, particularly for soft tissue, and eliminates artifacts due to broad x-ray spectra. Synchrotron sources are large and very expensive, however, and poorly suited for clinical use.

This is believed to be the first proposed use of CZT 2 sided strip detectors for computed tomography. This system will increase the spatial resolution by an order of magnitude over the only other reported dual x-ray CT/SPECT system. This system will extend the state of the art in multi energy computed tomography.

A method for simultaneous transmission x-ray computed tomography (CT) and single photon emission tomography (SPECT), in accordance with the inventive arrangements, comprises the steps of: injecting a subject with a tracer compound tagged with a γ-ray emitting nuclide; directing an x-ray source along an axis toward the subject; rotating the x-ray source around the subject; operating the x-ray source during the rotating step; rotating a cadmium zinc telluride (CZT) two-sided detector on an opposite side of the subject from the source; simultaneously detecting, with respect to position and energy, each pulsed x-ray and each emitted γ-ray captured by the CZT detector during the rotating; recording data indicative of each the position and each the energy of each the captured x-ray and γ-ray; and, creating respective CT and SPECT images from the recorded data. All of the steps can be implemented at ambient temperatures.

The method can further comprise the step of limiting the captured γ-rays to those of the γ-rays emitted along a predetermined set of projection angles, for example by collimating the γ-rays at a position in front of the detector. The projection angles can be normal to the detector.

The method can comprise the step of detecting and recording a pixel position, an angle of rotation and an energy level for each captured x-ray and γ-ray.

The scanner field of view can be set by adjusting the width of the detector in the plane of rotation.

The method can comprise the step of capturing the x-rays and γ-rays with an array of orthogonal stripes of the CZT. Biasing the stripes with an electric field, some of the stripes become anodes and the others of the stripes become cathodes, whereby electrons drift toward the anode stripes and holes drift toward the cathode stripes. The position of each captured x-ray and γ-ray can be established by determining which ones of the anode and cathode stripes carry a current pulse resulting from the captured x-ray or γ-ray.

The method can further comprise the steps of: determining ratios of electrical charge collected in adjacent ones of the stripes; and, determining each position based on the ratios.

The method can alternatively comprise the step of capturing the x-rays and γ-rays with an array of pixelated CZT detectors.

BRIEF DESCRIPTION OF THE DRAWINGS

There are shown in the drawings embodiments of the invention that are presently preferred, it being understood, however, that the invention is not limited to the precise arrangements and instrumentalities shown, wherein.

The scanner field of view is established by the width of the detector array 34 in the plane of rotation. The detector can be translated in this plane to increase the effective field of view during the rotation. Inasmuch as the presently preferred embodiment is intended for use with small animal studies, the entire apparatus 10 can rest on a table 40.

In the preferred embodiment, the system is configured so that the image resolution is established by the size of the pixels in the detector array. The presently preferred embodiment is designed for small animal studies so pixels on the order of 50 $\mu m^2$ are employed. A collimator can be placed in front of the detector to prevent scattered radiation from contributing to the image. When an x-ray CT image is acquired, the x-ray tube is turned on and data from the detector including pixel position, gantry angle of rotation and x-ray energy are transferred from the detector read-out electronics to a work station which in turn processes the data and generates a tomographic image.

When acquiring a SPECT image according to conventional methods, the x-ray tube is turned off and the subject is injected with a radioactive tracer compound which migrates to regions of interest within the subject. Gamma rays emitted by the tracer are collected by the detector and, as before, pixel position, gantry angle, and γ-ray energy data are transferred to the work station for image generation. SPECT acquisitions require a collimator in front of the detector to ensure that only γ-rays which are emitted normal to the detector, or along another predetermined set of projection angles, contribute to the energy.

In accordance with the inventive arrangements, X-ray CT and SPECT images can be simultaneously acquired if the x-ray tube is biased such that the x-ray energies are lower than the SPECT γ-ray energies. The CT and SPECT image data can be separated based upon energy parameters by the work station.

X-ray CT image generation in and of itself is explained in connection with FIG. 2. The x-ray CT produces 2-dimensional cross-sectional images of a subject by acquiring series of 1-dimensional x-ray projections from various positions around the subject. Each projection is a plot of the x-ray transmission I as a function of position on the detector surface u, such that, $$I(u) \exp[-\int \mu(u, v)dv]$$

where $\mu$ is the position dependent x-ray attenuation coefficient of the subject and v is the axis along which the x-ray travels through the subject. Thus, an x-ray CT projection is approximately a 1-dimensional map of the average linear attenuation coefficient of the subject along the axis of the incident x-rays.

Figure 1:
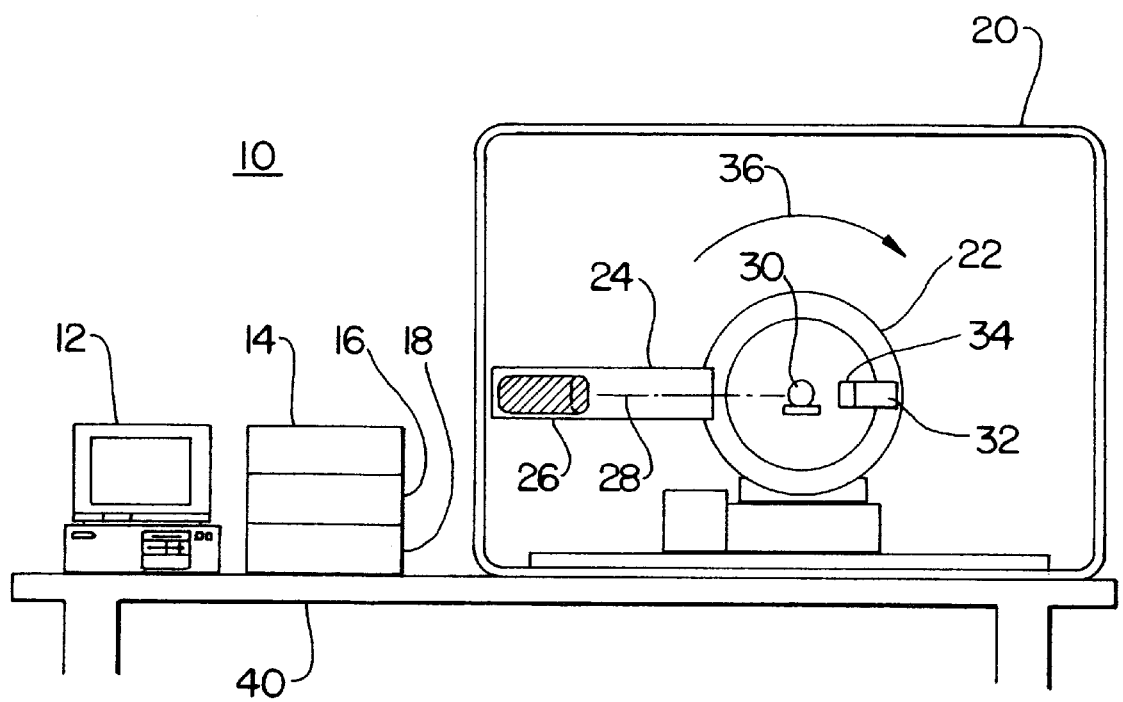
FIG. 1 is a schematic diagram of a computed tomography system suitable for simultaneous transmission x-ray computed tomography (CT) studies and single photon emission tomography (SPECT) in accordance with he inventive arrangements, and embodied for small animal studies.
Figure 2C:
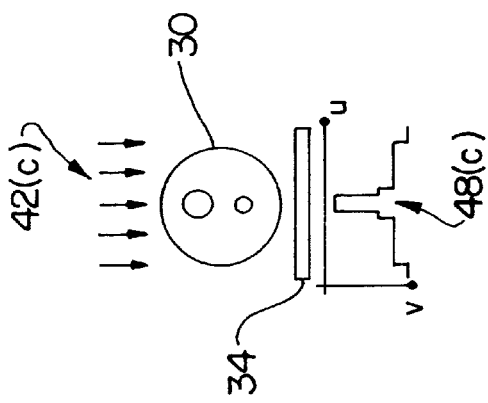
FIGS. 2(a), 2(b) and 2(c) illustrate three positions of the rotatable gantry and the corresponding projection data plots.
Figure 2B:
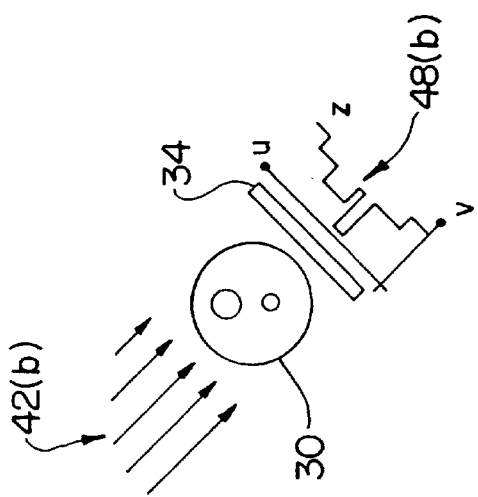
Figure 2A:
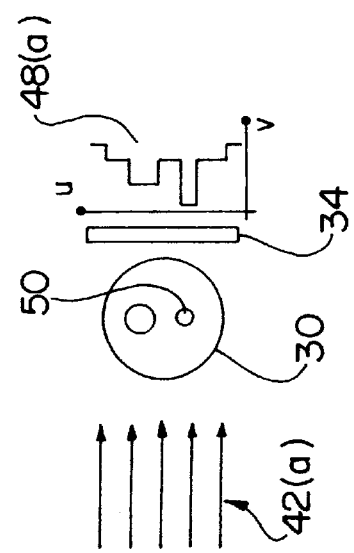

Once a family of projection data curves has been acquired, special algorithms are employed to reconstruct a 2-dimensional image or slice, as shown in FIGS. 2(a), 2(b) and 2(c) for three different angles of rotation of the gantry. The x-rays are denoted by reference numerals 42(a), 42(b) and 42(c) to distinguish the different angles. The three slices are represented by graphs or plots 48(a), 48(b) and 38(c). A 3-dimensional x-ray CT image can be obtained by combining multiple adjacent 2-dimensional slices. An x-ray CT image is therefore a first order volumetric map of the linear attenuation coefficient of the material in the subject.

Figure 3A:
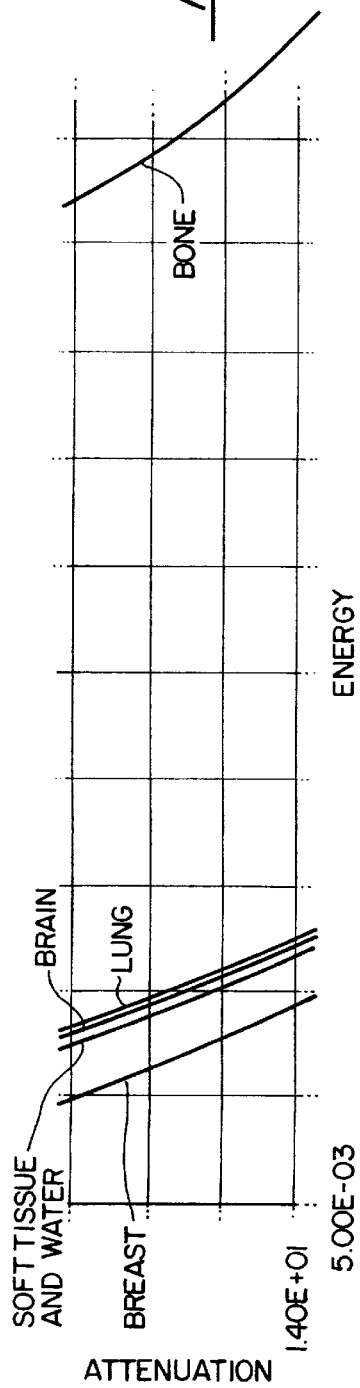
FIG. 3(a) is an enlarged portion of FIG. 3.
Figure 3:
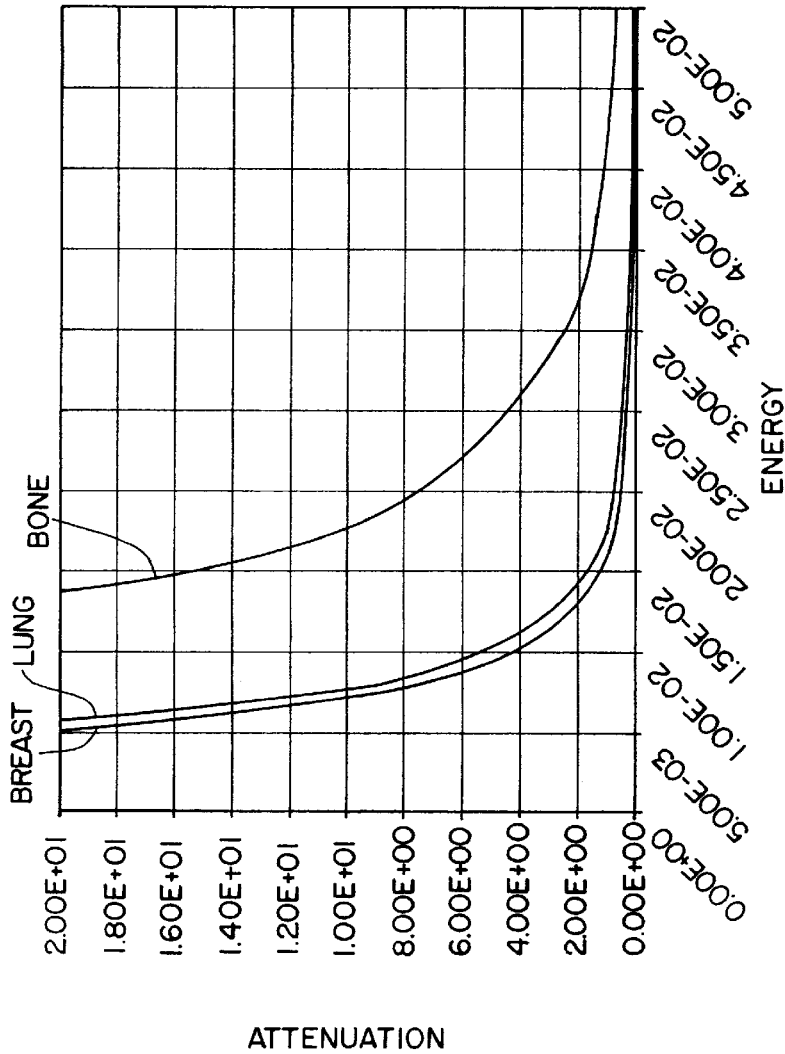
FIG. 3 is a graph useful for explaining energy dependent absorption coefficients for different tissue types.

In addition to being dependent upon the material composition under test, the measured attenuation coefficients are strongly dependent upon the energy of the x-rays used to generate the image. FIG. 3 shows the approximate energy dependent attenuation coefficients for six different types of tissue. The curves for breast tissue and bone tissue are easily distinguished in the scale of FIG. 3, but the other curves appear to overlap. FIG. 3(a) is an enlargement of a portion of FIG. 3, with an exaggerated horizontal scale, in which the remaining curves are better, although not completely distinguished. The curves for soft tissue and water substantially overlap one another. The curve for brain tissue is immediately to the right of the curve for soft tissue and water. The curve for lung tissue is immediately to the right of the curve for brain tissue. All of the curves except the curve for bone tissue converge in the lower right hand corner of the graph of FIG. 3. The choice of energy for a given x-ray CT study depends upon the type of tissue under study, the thickness and density of the object under study and the acceptable dose that the subject may absorb. For example, at low energies the attenuation coefficients are high and much of the radiation is absorbed by the subject. In order to image a thick subject (for example, a chest study) it may be necessary to use x-rays with energies in excess of 100 keV in order to avoid large patient exposure. The differences in attenuation coefficients between tissue types at high x-ray energies are rather small, however, so the choice of 100 keV x-rays limits the achievable image contrast. On the other hand, for mammography studies it is critical to differentiate between soft tissue and very small micro calcifications (the dominant component of bone tissue) so x-ray energies between 10 and 20 keV are typically used despite the increased dose. The dose is minimized by compressing the breast, a common complaint among patients. In order to achieve high contrast between different soft tissue types, it is desirable to minimize the x-ray energy in order to maximize the differences in attenuation coefficients. In order to differentiate between bone and all types of soft tissue, energies between 20 and 50 keV may be employed because the soft tissue attenuation is fairly constant over this energy range. For many studies two different x-ray energies are used (e.g. dual energy scans) and weighted values of the measured attenuation coefficients from the acquisition at one energy are subtracted from the second image. This approach exploits the energy dependent variations in the attenuation coefficients to obtain quantitative information regarding the tissue density.

Figure 4:
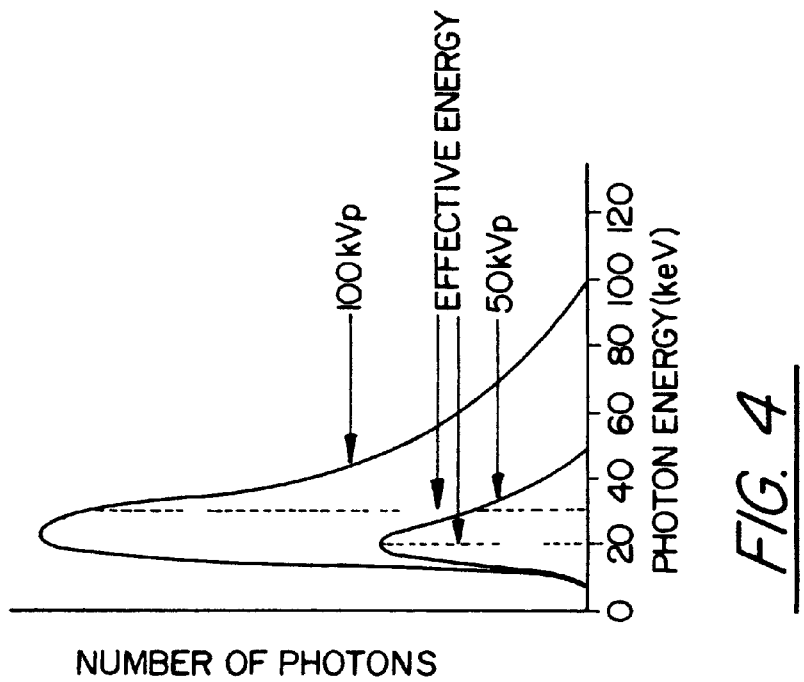
FIG. 4 is a graph useful for explaining an x-ray spectrum for a tube biased at 50 kVp and 100 kVp.

A significant limitation in traditional x-ray imaging techniques is the absence of monoenergetic x-ray sources for imaging. FIG. 4 shows schematically the shapes of typical x-ray tube emission spectra at two different voltages. The low energy x-ray intensity is determined by the composition and thickness of the filters between the x-ray source while the high energy intensity is determined by the operating voltage. As FIG. 4 shows, the x-ray spectra are far from monoenergetic. The calculated attenuation coefficients obtained in an x-ray study are therefore composite values for the range of x-ray energies used in the studies. The spread in the x-ray energies affects the image contrast and can introduce artifacts. As noted, the use of monoenergetic sources, for example a synchrotron x-ray source, improves image contrast, particularly for soft tissue, and eliminates artifacts due to broad x-ray spectra. However, synchrotron sources are large and very expensive, and poorly suited for clinical use.

The system taught herein measures the energy of each x-ray detected using a CZT detector and custom integrated readout electronics. A series of quasi-monoenergetic spectra can therefore be independently constructed and combined to achieve the benefits obtained by use of a synchrotron source. Additionally, because multiple images are acquired over a range of energies, multi-spectral analysis similar to those employed in dual energy studies can advantageously be performed with a single data acquisition.

Furthermore, unlike other pulse mode experiments which have been performed using HPGe detectors, the CZT detectors operate at room temperature and, because of the double sided strip configuration of the detector, the readout electronics are relatively sparse, permitting the design of very high spatial resolution detectors with physically realizable electronic architectures.

In a typical SPECT study the subject is injected with a tracer compound tagged with a γ-ray emitting nuclide such as Tc-99 m or Tl-201. The tracer compound emulates a biologically interesting compound in the subject and the image is a volumetric map of the tracer distribution in the subject.

Figure 5:
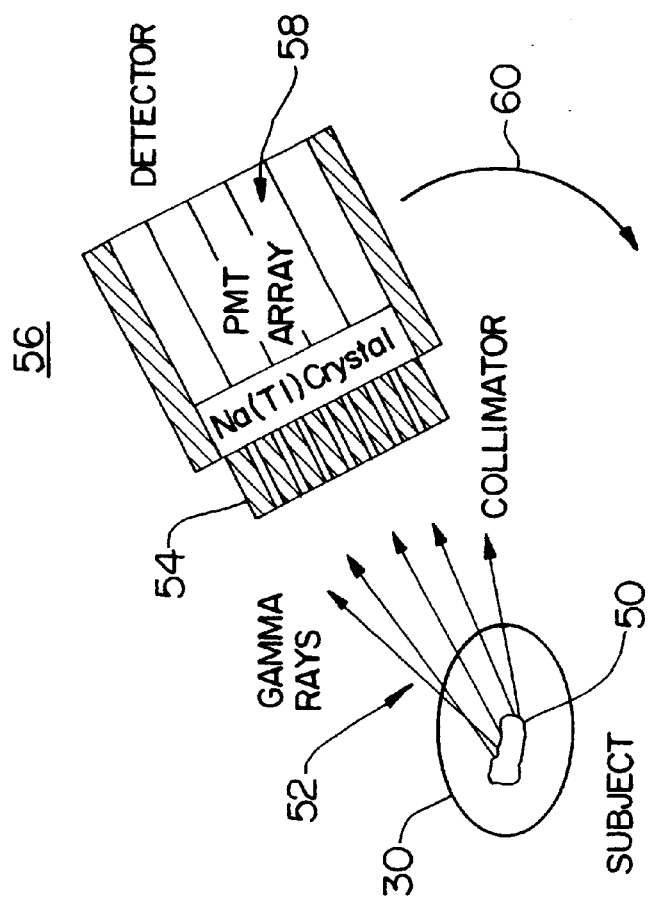
FIG. 5 is a schematic diagram useful for explaining a SPECT detector rotating about a subject injected with a γ-ray emitting tracer compound.

With reference to FIG. 5, typical SPECT nuclides 50 emit γ-rays 52 with energies ranging from approximately 75 keV to 250 keV. Clinical SPECT systems typically employ one or more angle detectors as shown in FIG. 5, each consisting of a single scintillator NaTl crystal 56 optically coupled to an array 58 of photo multiplier tubes (PMT) 58. These detectors are typically larger than 10 in². A collimator 54 is placed in front of the scintillator to ensure that only γ-rays traversing predetermined paths, typically normal to the detector, are collected. When a γ-ray is absorbed by the scintillator the resulting light is shared among the photo multiplier tubes in the array 58, the point of interaction can be determined by the ratios of the signals in the photo multiplier tubes. As with an x-ray CT system, the SPECT detector head is rotated about the subject, as indicated by arrow 60, so that multiple sets of projection data are acquired and a three dimensional map of the isotope distribution can be constructed.

The principal advantage of this detector configuration is that reasonable resolution (~5 mm) images can be acquired over large areas with large photo multiplier tubes (~2 in diameter) and relatively few electronic channels (~100). The disadvantages of this approach are that the entire detector can only process one γ-ray at a time, limiting the γ-ray throughput and the image statistics, and the resolution is poor compared with other modalities. Furthermore, this detector configuration is not suitable for simultaneous use with an x-ray source for dual modality studies due to the low throughput and limited resolution of the detector for low energy x-rays.

The system in accordance with the inventive arrangements employs CZT detectors suitable for imaging both lower energy x-ray and higher energy γ-rays. The strip detector described below provides resolutions on the order of 50 μm if adequate image statistics are available and has the potential for much higher data throughput if multiple detectors are used in parallel.

Figure 6:
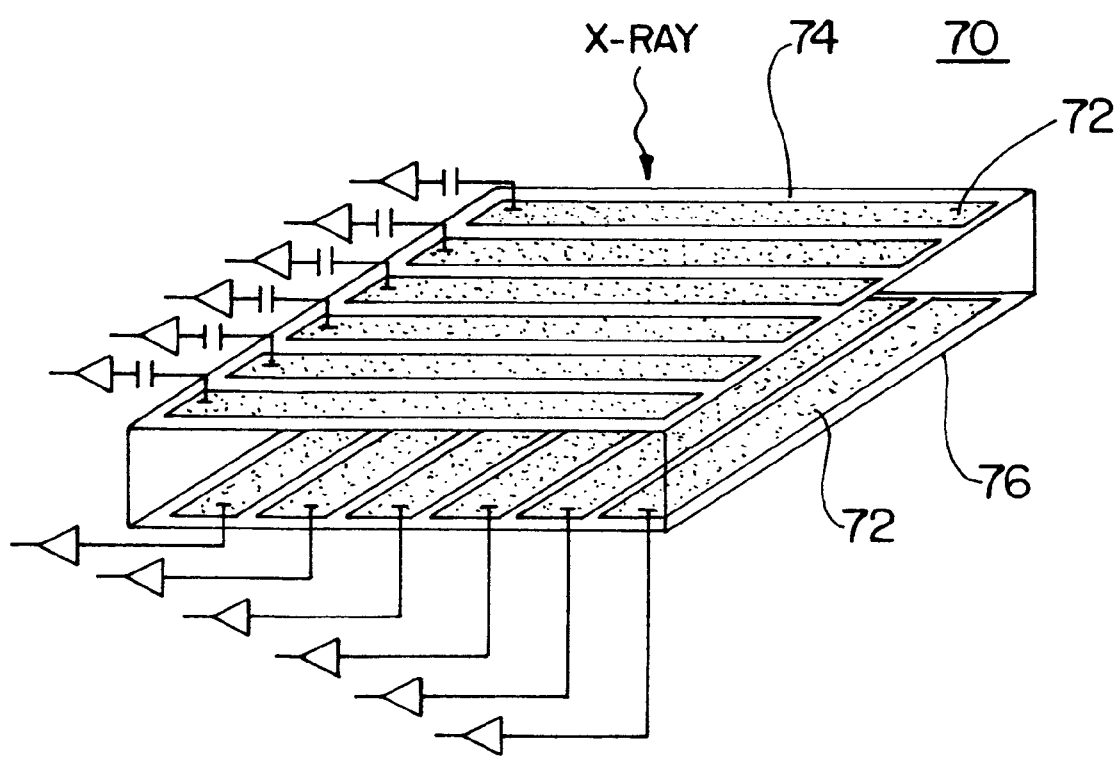
FIG. 6 is a schematic diagram of a CZT double sided semiconductor strip detector suitable for use with the inventive arrangements.

A CZT double sided strip detector (2SSD) 34 suitable for use with the inventive arrangements is shown in FIG. 6. The detector 34 comprises a CZT substrate patterned with orthogonal contact stripes 72 on the top 74 surface and the bottom surface 76. In normal operation the stripes are biased with an electric field between the cathode (top) and anode (bottom) stripes. When an incident x-ray or γ-ray is absorbed an ionization charge region is formed in the CZT consisting of mobile electrons and holes. The electrons drift toward the anode stripes while the holes drift toward the cathode stripes. By determining which anode and cathode stripes carry the resultant current pulse, the point at which the x-ray or γ-ray was absorbed is determined. Furthermore, by considering the ratio of charge collected in adjacent stripes, it is possible to determine the point of interaction with an accuracy of half the detector stripe spacing or better. The current state of the art for 2SSDs has the detector stripes patterned on a ~100 μm pitch, yielding an intrinsic resolution of 50 μm or less.

Figure 7:
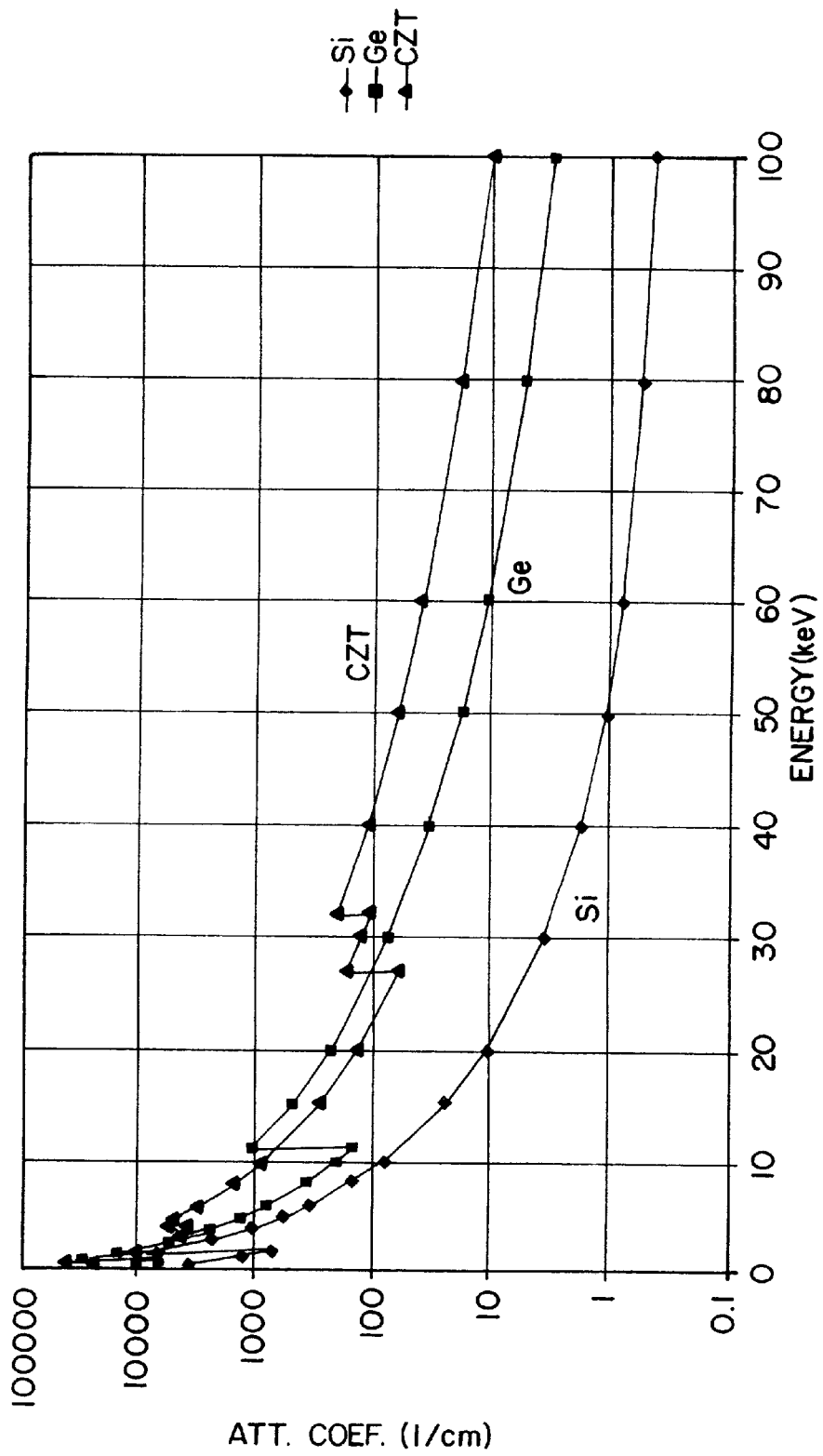
FIG. 7 is a graph useful for comparing linear attenuation coefficients for silicon, germanium and cadmium zinc telluride detector materials. DETAILED DESCRIPTION OF THE INVENTION The computed tomography system 10 in accordance with the inventive arrangements and shown in FIG. 1 is similar in many respects to industry standard third generation CT scanners. The system 10 comprises a computer work station 12, which interfaces with a gantry motion controller 14, the subject bed motion controller 16 and the x-ray tube high voltage supply and controller 16. The gantry is disposed inside of a radiation shielded protective enclosure 20. The protective enclosure 20 is preferably constructed of tin-doped plastic. The rotating gantry 22 has a first radial arm 24, outwardly directed, on which an x-ray emitting source 26 is disposed. The source is aimed so that x-rays emitted by the source are directed along axis 28 toward the subject 30. The gantry comprises a second radial arm 32, inwardly directed, on which a CZT detector array 34 is mounted. As the gantry rotates from the position shown in FIG. 1 in the direction of arrow 36, the subject under study is imaged with the x-rays over an arc of approximately 180 degrees, the subject always remaining positioned directly between the x-ray source and the detector array, all of which are aligned with axis 28. As will be explained in more detail, the subject can be injected with a γ-ray emitting tracer compound which collects in an area of the subject to be studied. Gamma rays emitted by the tracer compound will also be captured by the detector array as the gantry rotates.

An important advantage of CZT over other semiconductor detector materials is its high atomic number (~49) compared with silicon (14) and germanium (32), resulting in superior photon stopping power, particularly at higher energies above the Cd and Te K-shell binding energies. FIG. 7 shows the calculated attenuation coefficients for Si, Ge and CZT over an energy range of 1 keV to 100 keV. At 40 keV, the CZT linear attenuation coefficient is 3.8 times greater than that of Ge and 78 times greater than that of Si. A second advantage of CZT is its large bandgap (1.6 eV) compared with silicon (1.1 eV) and germanium (0.6 eV)., This results in lower thermal leakage currents during room temperature operation. This advantage is particularly important in comparison with Ge which typically must be operated at cryogenic temperatures. The conversion-efficiency of CZT is reasonable (~4.5 eV per electron-hole pair) but poorer than that of silicon (3.61 eV per electron-hole pair) and germanium (2.98 eV per electron-hole pair at 77 K).

The detector can be embodied in other configurations. The detector be configured as a planer system for digital radiology, particularly mammography. The detector can be embodied as two detectors used for acquiring positron emission tomography images simultaneously with x-ray CT or SPECT or both. Arrays of the detectors can be used in parallel to increase the field of view and/or improve data throughput. Detectors with much finer pitch can be employed for x-ray CT microscopy. The resolution is limited only by the limits of semiconductor processing technology. Finally, pixelated CZT detectors can be used in place of the strip detectors.

In summary, a computed tomography system in accordance with the inventive arrangements is suitable for simultaneous transmission x-ray computed tomography (CT) studies and single photon emission tomography (SPECT) nuclear medicine studies. The system uses one or more double sided CZT strip detector arrays. The two types of measurements can be performed simultaneously and displayed in a single image. The system can acquire multi spectral x-ray CT images providing opportunities for data analysis techniques and correction for image artifacts and non-optimal soft-tissue differentiation due to the broad spectrum of x-rays emitted by standard x-ray tubes. The double sided strip detector configuration permits the use of very small pixels (~50 $\mu m^2$) with a reasonable number of electronic channels. The spatial resolution is increased by one order of magnitude over the only other reported dual CT/SPECT system.

Systems in accordance with the inventive arrangements can have many uses, including but not limited to phenotype screening in laboratory animal mutagenesis studies, other in vivo studies with laboratory animals, drug discovery research using laboratory animals, medical imaging for human patients in a larger system, screening of electrical and mechanical components for defect identification, luggage screening contraband in a larger system and screening for weapons and explosives.

What is claimed is:

1. A method for simultaneous transmission x-ray computed tomography (CT) and single photon emission tomography (SPECT), comprising the steps of:

injecting a subject with a tracer compound tagged with a γ-ray emitting nuclide;
   directing and x-ray source along an axis toward said subject;
   rotating said x-ray source around said subject;
   operating said x-ray source during said rotating step;
   rotating a single cadmium zinc telluride (CZT) two-sided detector on an opposite side of said subject from said source;
   simultaneously detecting, with respect to position and energy, each pulsed x-ray and each emitted γ-ray captured by said single CZT detector during said rotating;
   recording data indicative of each said position and each said energy of each said captured x-ray and α-ray; and,
   creating respective CT and SPECT images from said recorded data.

2. The method of claim 1, further comprising the step of operating said x-ray source in a continuous mode.

3. The method of claim 2, further comprising the step of biasing transmitted energy levels of said x-rays lower than energy levels of said γ-rays.

4. The method of claim 1, further comprising the step of biasing transmitted energy levels of said x-rays lower than energy levels of said γ-rays.

5. The method of claim 1, comprising the step of implementing all said steps at ambient room temperatures.

6. The method of claim 2, comprising the step of implementing all said steps at ambient room temperatures.

7. The method of claim 3, comprising the step of implementing all said steps at ambient room temperatures.

8. The method of claim 4, comprising the step of implementing all said steps at ambient room temperatures.

9. The method of claim 1, further comprising the step of limiting said captured γ-rays to those of said γ-rays emitted along a predetermined set of projection angles.

10. The method of claim 9, comprising the step of collimating said γ-rays at a position in front of said detector.

11. The method of claim 9, wherein said projection angles are normal to said detector.

12. The method of claim 1, comprising the step of detecting and recording a pixel position, an angle of rotation and an energy level for each captured x-ray and γ-ray.

13. The method of claim 1, further comprising the step of fixing a scanner field of view by adjusting the width of the detector in the plane of rotation.

14. The method of claim 1, comprising the step of capturing the x-rays and γ-rays with an array of orthogonal stripes of said CZT.

15. The method of claim 14, further comprising the step of biasing the stripes with an electric field, some of said stripes becoming anodes and the others of said stripes becoming cathodes, whereby electrons drift toward said anode stripes and holes drift toward said cathode stripes.

16. The method of claim 15, further comprising the step of establishing the position at which each said x-ray and γ-ray is captured by determining which ones of said anode and cathode stripes carry a current pulse resulting from said captured x-ray or γ-ray.

17. The method of claim 16, further comprising the steps of:

determining ratios of electrical charge collected in adjacent ones of said stripes; and,
   determining each said position based on said ratios.

18. The method of claim 7, comprising the step of capturing the x-rays and γ-rays with an array of orthogonal stripes of said CZT.

19. The method of claim 18, further comprising the step of biasing the stripes with an electric field, some of said stripes becoming anodes and the others of said stripes becoming cathodes, whereby electrons drift toward said anode stripes and holes drift toward said cathode stripes.

20. The method of claim 19, further comprising the step of establishing the position at which each said x-ray and γ-ray is captured by determining which ones of said anode and cathode stripes carry a current pulse resulting from said captured x-ray or γ-ray.

21. The method of claim 20, further comprising the steps of:
   determining ratios of electrical charge collected in adjacent ones of said stripes; and,
   determining each said position based on said ratios.

22. The method of claim 1, comprising the step of capturing the x-rays and γ-rays with an array of pixelated CZT detectors.

23. The method of claim 4, comprising the step of capturing the x-rays and γ-rays with an array of pixelated CZT detectors.

24. The method of claim 7, comprising the step of capturing the x-rays and γ-rays with an array of pixelated CZT detectors.

25. A system for simultaneous transmission x-ray computed tomography (CT) and single photon emission tomography (SPECT), comprising:
   a radiation source for directing radiation toward a target;
   a single cadmium zinc telluride (CZT) two-sided detector disposed on an opposite side of said target from said radiation source;
   a structure for rotating said radiation source and said single CZT two-sided detector relative to said target, wherein said single CZT two-sided detector simultaneously detects, with respect to position and energy, each pulsed x-ray and each emitted γ-ray captured during said rotating, and
   a structure for creating respective CT and SPECT images from said pulsed x-ray and said γ-ray data.

26. A method for x-ray computed tomography (CT), comprising the steps of:
   directing an x-ray source along an axis toward a subject;
   rotating said x-ray source around said subject;
   operating said x-ray source during said rotating step;
   rotating a cadmium zinc telluride (CZT) two-sided detector on an opposite side of said subject from said source;
   detecting emitted radiation captured by said CZT detector during said rotating;
   recording data from said emitted radiation, and, creating a CT image from said recorded data.

* * * * *